(12) United States Patent
Aucouturier et al.

(10) Patent No.: US 7,815,910 B2
(45) Date of Patent: Oct. 19, 2010

(54) VACCINE COMPOSITION AND USE OF SURFACTANTS AS ADJUVANTS OF IMMUNITY

(75) Inventors: Jérôme Aucouturier, Chatenay Malabry (FR); Vincent Ganne, La Varenne Saint Hilaire (FR); Gérard Trouve, Castres (FR)

(73) Assignee: Societe d'Exploitation de Produits pour les Industries Chimiques, SEPPIC, Paris (FR)

( * ) Notice: Subject to any disclaimer, the term of this patent is extended or adjusted under 35 U.S.C. 154(b) by 267 days.

(21) Appl. No.: 12/061,514

(22) Filed: Apr. 2, 2008

(65) Prior Publication Data

US 2008/0187552 A1 Aug. 7, 2008

Related U.S. Application Data

(62) Division of application No. 09/698,121, filed on Oct. 30, 2000, now Pat. No. 7,422,748.

(30) Foreign Application Priority Data

Oct. 29, 1999 (FR) ................................... 99 13618

(51) Int. Cl.
*A61K 39/00* (2006.01)
*A61K 39/38* (2006.01)

(52) U.S. Cl. ................. 424/185.1; 424/184.1; 536/1.11
(58) Field of Classification Search ................. None
See application file for complete search history.

(56) References Cited

U.S. PATENT DOCUMENTS

| 3,678,149 A | 7/1972 | Prigal |
| 5,424,067 A | 6/1995 | Brancq et al. |
| 6,103,770 A | 8/2000 | Trouve |
| 6,117,432 A | 9/2000 | Ganne |
| 6,274,149 B1 | 8/2001 | Ganne |
| 7,422,748 B1 | 9/2008 | Aucouturier et al. |

OTHER PUBLICATIONS

Abstract for Griffin, W.C. "Calculation of HLB Values of Non-Ionic Surfactants", *Journal of the Society of Cosmetic Chemists 5*, 259. (1954).
Brancq et al., Abstract of FR 2649012 "Injectable Multi-Phase Emulsions", esp@cenet Database Worldwide (Jan. 1991).
Ganne et al., Abstract of FR 2755715, "Adjuvant, Notamment Sous Forme D'Une Emulsion Contenant Un Cation Metallique Trivalent Et Composition Vaccinale Le Comprenant (A1 B1) Adjuvant, Notamment Sous Forme D'Une Emulsion Contenant Un Cation Metallique Trivalent Et Composition Vaccinale Le Comprenant" esp@cenet Database Worldwide (Apr. 1998).
Ganne, Abstract of FR 2733151 "Therapeutic Composition Comprising an Antigen or an in Vivo Generator of a Compound Comprising an Amino Acid Sequence", esp@cenet Database Worldwide (Oct. 1996).
Garrett, P. R., "Defoaming: Theory and Industrial Applications, *Surfactant Science Series*"; vol. 45, p. 300, Marcel Dekker Inc., New York, New York (1993).
O'Neil et al., J Pharm Science vol. 61 (6): 863, (1972).
Perlaza, et al., Infec. & Immun., vol. 66, No. 6, pp. 3423-3428, (1972).
Trouve, Abstract of FR 2729307 "Utilization of Ethoxylated Fatty Acid Esters as Self-Emulsifiable Compounds", esp@cenet Database Worldwide (Jul. 1996).
Unknown, The Thesaurus of Chemical Products, vol. II: Tradename to Generic, pp. 64, and 283-284, Chemical Publishing Company, New York, New York (1986).

*Primary Examiner*—G. R Ewoldt
(74) *Attorney, Agent, or Firm*—Hunton & Williams LLP

(57) ABSTRACT

A composition comprising an aqueous solution comprising:
(i) at least one antigen or at least one in vivo generator of a compound comprising an amino acid sequence, and
(ii) as an adjuvant of immunity, a surfactant, or a mixture of surfactants, having an overall HLB number of between 5 and 15.

5 Claims, No Drawings

VACCINE COMPOSITION AND USE OF SURFACTANTS AS ADJUVANTS OF IMMUNITY

CROSS-REFERENCE TO RELATED APPLICATION

The present application is a divisional application of U.S. application Ser. No. 09/698,121, filed Oct. 30, 2000, now U.S. Pat. No. 7,422,748, which claims the benefit under 35 U.S.C. §119 of FR 9913618 filed in France on Oct. 29, 1999, the disclosures of which are hereby incorporated by reference.

BACKGROUND OF THE INVENTION (i) Field of the Invention

The present invention relates to novel adjuvants for vaccine compositions, and to compositions comprising at least one antigen, in particular an antigen of viral, bacterial or parasitic origin, and at least one adjuvant.

(ii) Description of the Related Art

The development of inactivated vaccines or vaccines containing purified antigens is increasingly significant, since it makes it possible to avoid adverse side effects. However, the improvement in the quality of the antigens occurs to the detriment of their immunogenic nature. It is for this reason that they are combined with adjuvants of immunity.

Adjuvants of immunity are products which increase the reactions of the immune system, when they are administered in the presence of antigens of viral, bacterial or synthetic origin. They cause a massive appearance of macrophages at the site of injection, and then in the lymph nodes, increase the production of specific immunoglobulins, antibodies, and stimulate many cells involved in immune defense mechanism.

These adjuvants are diverse in nature. They can, for example, consist of liposomes or emulsions.

Very effective Freund's adjuvants: they result from the combination of a mineral oil and of a mannitol ester, possibly containing a killed mycobacterium. Vaccines prepared by mixing in equal parts a Freund's adjuvant with an aqueous antigenic medium are still used as standards throughout the world for laboratory studies. They are in the form of water in oil (W/O) emulsions, i.e., emulsions in which the continuous phase is the oil. These emulsions are very viscous; they are thus difficult to inject; they are also relatively unstable, since phase displacements are observed only a few days after their preparation.

By way of ordinary adjuvants, there are also metal salts, such as aluminum hydroxide, cerium nitrate, zinc sulphate, colloidal iron hydroxide or calcium chloride. Of these, aluminum hydroxide is the most commonly used. These adjuvants are described in the article by Rajesh K. Gupta et al., "Adjuvants, balance between toxicity and adjuvanticity" Vaccine, Vol. 11, Issue 3, 1993, pages 993-1006. They exhibit, however, weak immunostimulatory effectiveness, and sometimes induce, when these therapeutic compositions are injected, the formation of lesions and other local reactions, such as granulomas, at the point of injection.

More recently, it has been discovered that water-soluble salts of divalent or trivalent metals are good adjuvants of immunity, in particular manganese gluconate, calcium gluconate, manganese glycerophosphate, soluble aluminum acetate and aluminum salicylate. Such adjuvants are described in the international patent applications published under the numbers WO 96/32964 and WO 98/17311.

As other adjuvants of immunity, in particular in the case of mucosal administration, mention may be made of the sympathomimetic compounds described in the international patent application published under the number WO 98/15288.

SUMMARY AND OBJECTS OF THE INVENTION

In the course of research into the development of novel adjuvants, the applicant has discovered that some surfactants themselves exhibit immunostimulatory effectiveness, and that it is thus possible to prepare aqueous vaccine compositions essentially free of oily phase, comprising one or more of these agents as an immunostimulant.

It is for this reason that the subject of the present invention is a composition in the form of an aqueous solution comprising:

(i) at least one antigen or at least one in vivo generator of a compound comprising an amino acid sequence, and (ii) as an adjuvant of immunity, a surfactant, or a mixture of surfactants, having an overall HLB number of between 5 and 15.

The term "antigen" or the phrase "at least one in vivo generator of a compound comprising an amino acid sequence" refers to either killed microorganisms, such as viruses, bacteria or parasites, or purified fractions of these microorganisms, or living microorganisms whose pathogenic power has been attenuated. As a virus which can constitute an antigen according to the present invention, mention may be made of rabies virus, herpes viruses, such as the virus of Aujeszky's disease, orthomixoviruses such as Influenzae, picornaviruses such as the virus of foot-and-mouth disease, or retroviruses such as HIVs. As microorganisms of the bacterial type which can constitute an antigen according to the present invention, mention may be made of *E. coli*, and those of the *Pasteurella, Furonculosis, Vibriosis, Staphylococcus* and *Streptococcus* genera. As parasites, mention may be made of the *Trypanosoma, Plasmodium* and *Leishmania* genera. Mention may also be made of recombinant viruses, in particular nonenveloped viruses such as adenoviruses, the vaccinia virus, the canarypox virus, herpes viruses or baculoviruses. Reference is also made to a living nonenveloped viral recombinant vector, the genome of which contains, inserted preferably into a portion which is nonessential for the replication of the corresponding enveloped virus, a sequence encoding an antigenic subunit which induces synthesis of antibodies and/or a protective effect against the above-mentioned pathogenic enveloped virus or microorganism; these antigenic subunits can be, for example, a protein, a glycoprotein, a peptide or a fraction which is a peptide and/or which is protective against an infection with a living microorganism such as an enveloped virus, a bacterium or a parasite. The exogenous gene inserted into the microorganism can be, for example, derived from an HIV or Aujeszky virus.

Mention may be made in particular of a recombinant plasmid consisting of a nucleotide sequence, into which is inserted an exogenous nucleotide sequence originating from a pathogenic microorganism or virus. The aim of the latter nucleotide sequence is to allow the expression of a compound comprising an amino acid sequence, the aim of this compound itself being to trigger an immune reaction in a host organism.

The expression "in vivo generator of a compound comprising an amino acid sequence" refers to an entire biological product capable of expressing said compound in the host organism into which said in vivo generator has been introduced. The compound comprising the amino acid sequence can be a protein, a peptide or a glycoprotein. These in vivo generators are generally obtained by methods derived from genetic engineering. More particularly, they can consist of living microorganisms, generally a virus, playing the role of recombinant vector, into which is inserted a nucleotide sequence, in particular an exogenous gene. These compounds are known in themselves, and are used in particular as recombinant subunit vaccines. In this respect, reference may be made to the article by M. Eloit et al., Journal of Virology (1990) 71, 2925-2431, and to the international patent applications published under the numbers WO-A-91/00107 and WO-A-94/16681. The in vivo generators according to the invention can also consist of a recombinant plasmid which comprises an exogenous nucleotide sequence, and which is capable of expressing, in a host organism, a compound comprising an amino acid sequence. Such recombinant plasmids and their method of administration to a host organism were described in 1990 by Lin et al., Circulation 82: 2217, 2221; Cox et al., J. of Virol., September 1993, 67, 9, 5665-5667, and in the international application published under the number WO 95/25542. Depending on the nature of the nucleotide sequence included in the in vivo generator, the compound comprising the amino acid sequence which is expressed within the host organism can:

(i) be an antigen, and enable the triggering of an immune reaction; (ii) have a curative action with respect to a disease, essentially a disease of a functional nature, which has been triggered in the host organism. In this case, the in vivo generator enables gene therapy type treatment of the host.

By way of example, such a curative action can consist of synthesis by the in vivo generator of cytokines, such as interleukins, in particular interleukin-2. These interleukins allow the triggering or the reinforcement of an immune reaction directed towards selective elimination of cancerous cells.

A composition according to the invention comprises an antigen concentration which depends on the nature of this antigen and on the nature of the individual treated. It is, however, particularly noteworthy that an adjuvant according to the invention makes it possible to notably decrease the conventional antigen dose required. The suitable antigen concentration can be determined conventionally by persons skilled in the art, Generally, this dose is about 0.1 µg/cm$^3$ to 1 g/cm$^3$, more generally between 1 µg/cm$^3$ and 100 mg/cm$^3$.

The concentration of said in vivo generator in the composition according to the invention depends, here again, in particular on the nature of said generator and of the host in which is administered. This concentration can be easily determined by persons skilled in the art, on the basis of routine experiment. By way of indication, it may, however, be specified that, when the in vivo generator is a recombinant microorganism, its concentration in the composition according to the invention can be between 10$^2$ and 10$^{15}$ microorganisms/cm$^3$, preferably between 10$^5$ and 10$^{12}$ microorganisms/cm$^3$. When the in vivo generator is a recombinant plasmid, its concentration in the composition according to the invention can be between 0.01 and 100 g/dm$^3$.

For the purpose of the present invention, the HLB number is calculated using the formula HLB=20 (1−$I_s$/$I_a$) in which $I_s$ represents the saponification index and $I_a$ represents the acid index of said surfactant or of said mixture of surfactants.

These two indices, saponification and acid indices, are determined by methods described in the European Pharmacopoeia.

The main subject of the invention is a composition as defined above, in which the surfactant(s) is (are) chosen from modified fatty substances and, preferably, the surfactants(s) is (are) chosen from modified fatty substances having an overall HLB number of between 6 and 14.

The modified fatty substances used in the context of the present invention can be of mineral, plant or animal origin. As modified fatty substances of mineral origin there are oils of petroleum origin. As modified fatty substances of plant origin, there are modified plant oils, for example modified groundnut, olive, sesame, soya bean, wheatgerm, grapeseed, sunflower, castor, flax, corn, copra, palm, walnut, hazelnut or rapeseed oils. As modified fatty substances of animal origin, there are, for example, modified squalane, modified squalene, modified spermaceti oil or modified tallow oil.

The term "modified fatty substances" refers in particular to the alkoxylated derivatives of fatty substances, and more particularly the alkoxylated derivatives of oils or the alkoxylated derivatives of alkyl esters of oils, and more particularly the ethoxylated and/or propoxylated derivatives of oils or the ethoxylated and/or propoxylated derivatives of the methyl, ethyl, linear or branched propyl, or linear or branched butyl esters of said oils. A subject of the invention is more specifically a composition as defined above, in which the modified fatty substance is chosen from the ethoxylated derivatives of oils having a number of EOs of between 1 and 60.

A subject of the invention is particularly a composition as defined above, in which the modified fatty substance is an alkoxylated derivative of corn oil, or a mixture of alkoxylated derivatives of corn oil, having an overall HLB number of between 10 and 14, or a composition as defined above in which the modified fatty substance is an ethoxylated derivative of castor oil, or a mixture of alkoxylated derivatives of castor oil, having an overall HLB number of between 7 and 10. As examples of such compositions, there is the composition in which the modified fatty substance is chosen from the ethoxylated derivatives of corn oil having a number of EOs of between 20 and 40, or the composition in which the modified fatty substance is a mixture of ethoxylated derivatives of castor oil having a number of EOs equal to 7 and of ethoxylated derivatives of castor oil having a number of EOs equal to 60.

A composition which is a subject of the present invention contains between 0.2 mg/cm$^3$ and 500 mg/cm$^3$ of adjuvant, more particularly between 2 mg/cm$^3$ and 500 mg/cm$^3$ of adjuvant and preferably between 50 mg/cm$^3$ and 200 mg/cm$^3$ of adjuvant.

According to a second specific aspect of the present invention, a subject of this invention is a composition as defined above, in which the surfactant(s) is (are) chosen from the alkoxylated derivatives of esters of fatty acids and of polyols or the alkoxylated derivatives of ethers of fatty alcohols and of polyols, and more particularly from alkoxylated fatty acid triglycerides, the polyglycerol alkoxylated esters of fatty acids, the alkoxylated esters of fatty acids with a hexol, such as for example sorbitol or mannitol, or the alkoxylated esters of fatty acids with a hexol anhydride, such as sorbitan or mannitan.

As fatty acids which are suitable for preparing these modified esters, there are more particularly those comprising from 12 to 22 carbon atoms, advantageously a fatty acid which is liquid at 20° C., such as for example those comprising from 16 to 18 carbon atoms, for instance oleic acid, ricinoleic acid or isostearic acid.

The composition as defined above contains in particular one or more ethoxylated derivatives of esters of fatty acids and of polyols, or the ethoxylated derivatives of ethers of fatty alcohols and of polyols, having a number of EOs of between 1 and 60. The surfactant, or the mixture of surfactants, of this composition as defined above has more particularly an overall HLB number of between 10 and 14, and preferably between 12 and 13. As an example of such a composition, there is the one in which the surfactant is an ethoxylated derivative of mannitan oleate having a number of Eos of between 5 and 15, and preferably between 7 and 11.

A surfactant according to the invention is preferably pharmaceutically acceptable for the mucous membranes; it must, in particular, be devoid of heavy metals and have very low acid or peroxide indices. It is also desirable for it to satisfy the standards of innocuity tests such as those described by S. S. Berllin, Annals of Allergy, 1962, 20, 473, or the abnormal toxicity tests described in the European Pharmacopoeia.

The composition according to the invention can comprise a conventional immunostimulant such as AVRIDINE®, N,N-dioctadecyl-N',N'-bis(2-hydroxy-ethyl)propanediamine, MDP (muramyl depeptide) derivatives, in particular threonyl-MDP, mycolic acid derivatives or Lipid A derivatives.

The composition according to the invention can comprises one or more water-soluble metal cation organic salts, such as for example calcium gluconate, manganese gluconate, aluminum salicylate or soluble aluminum acetate. When the adjuvant composition according to the invention comprises a pharmaceutically acceptable salt, this salt is at a concentration of 0.02 to 3000 mg/cm$^3$, preferably 0.1 to 1000 mg/cm$^3$, more preferably from 0.1 to 150 mg/cm$^3$.

The composition according to the invention can comprise a sympathomimetic compound. The term "sympathomimetic compounds" refers in particular to amphetamines, catecholamines, phenylisopropylamines and tyramine. As examples of such compounds mention may be made in particular of isoproterenol, L-adrenalin, levarterenol, ephedrine, phenylephedrine and salbutamol When the adjuvant composition according to the invention comprises a sympathomimetic compound, this compound is at a concentration of $10^{-10}$ molar to $10^{-2}$ molar, preferably from $10^{-7}$ molar to $10^{-5}$ molar.

The use of surfactants as defined above as adjuvants in the vaccine compositions, and more particularly in the vaccine compositions which have no oily phase, constitutes another aspect of the present invention.

The composition according to the invention can be used as a preventive or curative medicinal product. Depending on the nature of the antigen or of the in vivo generator, a composition according to the invention can be administered to fish, crustaceans such as shrimps, poultry, in particular geese, turkeys, pigeons and chickens, to Canidae such as dogs, to Felidae such as cats, to pigs, to primates, to Bovidae, to Ovidae and to horses. The composition according to the invention can also be administered to humans. The administration of the composition can be carried out conventionally via the parenteral route, in particular by subcutaneous, intramuscular or intraperitoneal injection, or via the mucosal route, in particular orally, rectally, nasally or vaginally. According to another aspect of the invention, it consists of the use of an adjuvant as defined above for preparing a vaccine intended for preventing or for treating an infectious disease, in particular an infectious disease engendered by a virus or a microorganism, such as those mentioned above.

According to another final aspect of the present invention, it consists of the use of this adjuvant for preparing a composition intended to treat a disease of a functional nature, such as cancer or cystic fibrosis.

EXAMPLE 1

100 microliters of various compositions containing a surfactant, phosphate buffer (PBS) and 10 mg/cm$^3$ of ovalbumin were injected subcutaneously into various batches of 5 female mice of the OF1 strain, weighing an average of 18 to 20 grams, at t=0 with a booster at t=28 days.

Blood samples are taken at 14, 28, 42, 56, 90 and 180 days.

ELISA assays are carded out on the blood samples, for IgG1s in order to determine the humoral immune response, and IgG2as in order to determine the cellular immune response. Local reactions were evaluated at 7 days and at 35 days.

The compositions are as follows:

| Surfactant used (SA) (Composition) weight % | HLB of SA | SA in μl | Buffer (PBS) in μl | Antigen (10 mg/cm$^3$) in μl |
|---|---|---|---|---|
| Ethoxylated corn oil (3 EOs) (Reference 1) | 4.1 | 100 | 1900 | 20 |
| Ethoxylated corn oil (10 EOs) + glycerol at 2% of initial load (Composition A) | 7.9 | 100 | 1900 | 20 |
| Ethoxylated corn oil (20 EOs) + glycerol at 2% of initial load (Composition B) | 10.4 | 100 | 1900 | 20 |
| Ethoxylated corn oil (30 EOs) + glycerol at 2% of initial load (Composition C) | 12.3 | 100 | 1900 | 20 |
| Ethoxylated corn oil (40 EOs) + glycerol at 2% of initial load (Composition D) | 13.8 | 100 | 1900 | 20 |
| Ethoxylated corn oil (20 EOs) + glycerol at 4% of initial load (Composition E) | 14.2 | 100 | 1900 | 20 |
| Ethoxylated corn oil (40 EOs) + glycerol at 4% of initial load (Composition F) | 11.3 | 100 | 1900 | 20 |
| Mannitan oleate (5 EOs) (Composition G) | 10.9 | 100 | 1900 | 20 |
| Mannitan oleate (8 EOs) (Composition H) | 12.4 | 100 | 1900 | 20 |
| Mannitan oleate (10 EOs) (Composition I) | 13.1 | 100 | 1900 | 20 |
| Mannitan oleate (15 EOs) (Composition J) | 14.6 | 100 | 1900 | 20 |
| Mannitan oleate (20 EOs) (Composition K) | 15.6 | 100 | 1900 | 20 |
| Mannitan oleate (40 EOs) (Composition L) | 17.3 | 100 | 1900 | 20 |
| Mannitan oleate (Reference 2) | 3.3 | 100 | 1900 | 20 |
| Mannitan oleate (8 EOs) (Composition M) | 12.1 | 100 | 1900 | 20 |
| Mannitan oleate + mannitan oleate (8 EOs) (Composition N) | 6.5 | 100 | 1900 | 20 |
| Mannitan oleate + mannitan oleate (8 EOs) (Composition O) | 5.0 | 100 | 1900 | 20 |
| Manganese gluconate (Reference 3) | — | 200 | 1800 | 20 |
| Control | — | 0 | 2000 | 20 |

The results of the ELISA assays are as follows:

| Composition | IgG1 assay (timescale in days) | | | | | |
|---|---|---|---|---|---|---|
| | D14 | D28 | D42 | D56 | D90 | D180 |
| Reference (1) | 1500 | 1000 | 32000 | 48000 | 32000 | 6000 |
| Composition (A) | 1000 | 1000 | 8000 | 12000 | 3000 | 1500 |
| Composition (B) | 1000 | 1000 | 64000 | 64000 | 16000 | 8000 |
| Composition (C) | 2000 | 1000 | 96000 | 128000 | 128000 | 12000 |
| Composition (D) | 1500 | 1000 | 6000 | 32000 | 64000 | 6000 |
| Composition (E) | 1000 | 1000 | 32000 | 64000 | 96000 | 24000 |
| Composition (F) | 3000 | 8000 | 64000 | 128000 | 128000 | 32000 |
| Composition (G) | 2000 | 2000 | 8000 | 64000 | 48000 | 8000 |
| Composition (H) | 4000 | 8000 | 128000 | 128000 | 48000 | 16000 |
| Composition (I) | 4000 | 1000 | 128000 | 96000 | 48000 | 12000 |
| Composition (J) | 1000 | 2000 | 64000 | 24000 | 6000 | 2000 |
| Composition (K) | 1000 | 1000 | 24000 | 12000 | 2000 | 2000 |
| Composition (L) | 1000 | 1000 | 18000 | 6000 | 2000 | 2000 |
| Reference (2) | 1000 | 1000 | 32000 | 16000 | 3000 | 2000 |
| Composition (M) | 4000 | 4000 | 128000 | 128000 | 256000 | 48000 |
| Composition (N) | 1500 | 1000 | 128000 | 64000 | 32000 | 12000 |
| Composition (O) | 1000 | 1000 | 32000 | 20000 | 16000 | 2000 |
| Reference (3) | 32000 | 32000 | 256000 | 128000 | 32000 | 8000 |
| Control | 1000 | 1000 | 4000 | 2000 | 3000 | 1000 |

| Composition | IgG2a assay (timescale in days) | | | | | |
|---|---|---|---|---|---|---|
| | D14 | D28 | D42 | D56 | D90 | D180 |
| Reference (1) | 1000 | 1000 | 1000 | 1500 | 3000 | 1000 |
| Composition (A) | 1000 | 1000 | 1000 | 1000 | 2000 | 1000 |
| Composition (B) | 1000 | 1000 | 2000 | 2000 | 2000 | 1000 |
| Composition (C) | 1000 | 1000 | 4000 | 1500 | 3000 | 1000 |
| Composition (D) | 1000 | 1000 | 1000 | 2000 | 4000 | 1000 |
| Composition (E) | 1000 | 1000 | 1000 | 2000 | 4000 | 1000 |
| Composition (F) | 1000 | 1000 | 1000 | 6000 | 4000 | 1000 |
| Composition (G) | 1000 | 1000 | 1000 | 8000 | 3000 | 100 |
| Composition (H) | 1000 | 1000 | 1000 | 3000 | 3000 | 1000 |
| Composition (I) | 1000 | 1000 | 4000 | 3000 | 2000 | 1000 |
| Composition (J) | 1000 | 1000 | 3000 | 1500 | 2000 | 1000 |
| Composition (K) | 1000 | 1000 | 1000 | 1500 | 2000 | 1000 |
| Composition (L) | 1000 | 1000 | 1000 | 1500 | 2000 | 1000 |
| Reference (2) | 1000 | 1000 | 1000 | 1500 | 3000 | 1000 |
| Composition (M) | 1000 | 1000 | 4000 | 1500 | 6000 | 1000 |
| Composition (N) | 1000 | 1000 | 4000 | 1500 | 2000 | 1000 |
| Composition (O) | 1000 | 1000 | 4000 | 1500 | 6000 | 1000 |
| Reference (3) | 1000 | 1000 | 4000 | 16000 | 2000 | 1000 |
| Control | 1000 | 1000 | 1000 | 1000 | 1000 | 1000 |

EXAMPLE 2

The procedure is carried out in the same way as in Example 1, with the following ethoxylated castor oils as surfactants:

| Surfactant used (SA) (Composition) weight % | HLB of SA | SA in µl | Buffer (PBS) in µl | Antigen (10 mg/cm$^3$) in µl |
|---|---|---|---|---|
| Ethoxylated castor oil 100% (7 EOs) (Composition P) | 6 | 100 | 1900 | 20 |
| Ethoxylated castor oil 89.13% (7 EOs) + 10.87% (60EOs) (Composition Q) | 7 | 100 | 1900 | 20 |
| Ethoxylated castor oil 78.26% (7 EOs) + 21.74% (60EOs) (Composition R) | 8 | 100 | 1900 | 20 |
| Ethoxylated castor oil 67.39% (7 EOs) + 32.61% (60EOs) (Composition S) | 9 | 100 | 1900 | 20 |
| Ethoxylated castor oil 56.52% (7 EOs) + 43.487% (60 EOs) (Composition T) | 10 | 100 | 1900 | 20 |
| Ethoxylated castor oil 50% (7 EOs) + 50% (60 EOs) (Composition U) | 10.6 | 100 | 1900 | 20 |
| Ethoxylated castor oil 45.65% (7 EOs) + 54.35% (60 EOs) (Composition V) | 11 | 100 | 1900 | 20 |
| Ethoxylated castor oil 34.78% (7 EOs) + 65.22% (60EOs) (Composition W) | 12 | 100 | 1900 | 20 |
| Ethoxylated castor oil 23.91% (7 EOs) + 76.09% (60 EOs) (Composition X) | 13 | 100 | 1900 | 20 |
| Ethoxylated castor oil 13.04% (7 EOs) + 86.96% (60 EOs) (Composition Y) | 14 | 100 | 1900 | 20 |
| Mannitan oleate (15 EOs) (Composition J) | 14.6 | 100 | 1900 | 20 |
| Ethoxylated castor oil 100% (60EOs) (Composition Z) | 15.2 | 100 | 1900 | 20 |
| Control (C1) | | 1000 | 1000 | 20 |
| Control (C2) | | 0 | 2000 | 20 |

The results of the ELISA assays are as follows:

| Composition | IgG1 assay (timescale in days) | | | | | |
|---|---|---|---|---|---|---|
| | D14 | D28 | D42 | D56 | D90 | D180 |
| Composition (P) | 1600 | 600 | 8000 | 16000 | 12000 | nd |
| Composition (Q) | 3200 | 600 | 16000 | 64000 | 48000 | nd |
| Composition (R) | 2400 | 400 | 48000 | 64000 | 64000 | nd |
| Composition (S) | nd | nd | nd | nd | nd | nd |
| Composition (T) | 600 | 100 | 16000 | 32000 | 32000 | nd |

-continued

| Composition | IgG1 assay (timescale in days) | | | | | |
|---|---|---|---|---|---|---|
| | D14 | D28 | D42 | D56 | D90 | D180 |
| Composition (U) | 100 | 100 | 8000 | 32000 | 32000 | nd |
| Composition (V) | 100 | 100 | 8000 | 12000 | 6000 | nd |
| Composition (W) | nd | nd | nd | nd | nd | nd |
| Composition (X) | 200 | 100 | 3000 | 4000 | 3000 | nd |
| Composition (Y) | 400 | 100 | 4000 | 12000 | 8000 | nd |
| Composition (Z) | 100 | 100 | 8000 | 6000 | 6000 | nd |
| Control (C1) | 19200 | 12800 | 256000 | 128000 | 128000 | nd |
| Control (C2) | 100 | 100 | 4000 | 2000 | 1500 | nd |

| Composition | IgG2a assay (timescale in days) | | | | | |
|---|---|---|---|---|---|---|
| | D14 | D28 | D42 | D56 | D90 | D180 |
| Composition (P) | 100 | 100 | 8000 | 3000 | 3000 | nd |
| Composition (Q) | 100 | 100 | 1200 | 4000 | 8000 | nd |
| Composition (R) | 100 | 100 | 32000 | 8000 | 8000 | nd |
| Composition (S) | nd | nd | nd | nd | nd | nd |
| Composition (T) | 100 | 100 | 16000 | 3000 | 8000 | nd |
| Composition (U) | 100 | 100 | 6000 | 4000 | 4000 | nd |
| Composition (V) | 100 | 100 | 4000 | 15000 | 2000 | nd |
| Composition (W) | nd | nd | nd | nd | nd | nd |
| Composition (X) | 100 | 100 | 1000 | 1000 | 1000 | nd |
| Composition (Y) | 100 | 100 | 1000 | 1000 | 1000 | nd |
| Composition (Z) | 100 | 100 | 1000 | 1000 | 3000 | nd |
| Control C1 | 100 | 100 | 8000 | 3000 | 8000 | nd |
| Control C2 | 100 | 100 | 1000 | 1000 | 1000 | nd |

What is claimed is:

1. A vaccine comprising:
   (i) at least one antigen or at least one in vivo generator of a compound comprising an amino acid sequence, and
   (ii) a surfactant, or a mixture of surfactants, having an overall HLB number of between 5 and 15 and comprising:
      ethoxylated derivatives of ester of fatty acids having 12 to 22 carbon atoms with sorbitan or mannitan having a number of EOs of between 1 and 60; or
      ethoxylated derivatives of oils having a number of EOs of between 1 and 60.

2. The vaccine as defined in claim 1, wherein said vaccine does not include an oily phase.

3. The vaccine as defined in claim 1, wherein said vaccine is suitable for mucosal vaccination.

4. The vaccine as defined in claim 1, wherein said vaccine suitable for application orally, nasally, rectally, or vaginally.

5. The vaccine of claim 1, wherein said surfactant or said mixture of surfactants comprises:
   ethoxylated derivatives of mannitan oleate having a number of EOs of between 5 and 15;
   ethoxylated derivates of corn oil having a number of EOs between 20 and 40; or
   ethoxylated derivatives of castor oil having a number of ECs equal to 7 or equal to 60.

* * * * *